US009470652B1

(12) United States Patent
Hooper et al.

(10) Patent No.: US 9,470,652 B1
(45) Date of Patent: Oct. 18, 2016

(54) SENSING FIELD EFFECT TRANSISTOR DEVICES AND METHOD OF THEIR MANUFACTURE

(71) Applicant: FREESCALE SEMICONDUCTOR, INC., Austin, TX (US)

(72) Inventors: Stephen R. Hooper, Mesa, AZ (US); Leo M. Higgins, III, Austin, TX (US); Raymond M. Roop, Paradise Valley, AZ (US)

(73) Assignee: Freescale Semiconductor, Inc., Austin, TX (US)

( * ) Notice: Subject to any disclaimer, the term of this patent is extended or adjusted under 35 U.S.C. 154(b) by 0 days.

(21) Appl. No.: 14/854,265

(22) Filed: Sep. 15, 2015

(51) Int. Cl.
*H01L 21/00* (2006.01)
*G01N 27/414* (2006.01)

(52) U.S. Cl.
CPC ...... *G01N 27/4148* (2013.01); *G01N 27/4145* (2013.01)

(58) Field of Classification Search
None
See application file for complete search history.

(56) References Cited

U.S. PATENT DOCUMENTS

| | | | | |
|---|---|---|---|---|
| 4,874,499 | A * | 10/1989 | Smith | G01N 27/414 156/60 |
| 5,078,855 | A * | 1/1992 | Mochizuki | G01N 27/414 204/412 |
| 5,138,251 | A * | 8/1992 | Koshiishi | G01N 27/414 204/416 |
| 6,236,075 | B1 * | 5/2001 | Hsiung | G01N 27/414 204/411 |
| 6,399,418 | B1 * | 6/2002 | Glenn | H01L 21/561 257/E23.069 |
| 6,420,201 | B1 * | 7/2002 | Webster | G01L 9/0054 257/E21.504 |
| 6,432,737 | B1 * | 8/2002 | Webster | B81B 7/0077 257/419 |
| 7,906,859 | B2 * | 3/2011 | Yoshioka | H01L 23/3107 257/788 |
| 8,536,626 | B2 | 9/2013 | Brown et al. | |
| 2009/0194427 | A1 * | 8/2009 | Hsiung | G01N 27/3335 205/414 |
| 2012/0228756 | A1 * | 9/2012 | Kolleth | H01L 23/16 257/708 |
| 2012/0273845 | A1 * | 11/2012 | Brown | G01N 27/414 257/253 |
| 2013/0069120 | A1 * | 3/2013 | Merz | G01N 27/4148 257/253 |
| 2015/0028395 | A1 * | 1/2015 | Horkheimer | B32B 37/1292 257/253 |
| 2015/0276663 | A1 * | 10/2015 | Takechi | G01N 27/414 257/253 |

OTHER PUBLICATIONS

Jimenez-Jorquera et al, "ISFET Based Microsensors for Environmental Monitoring", Sensors 2010, Dec. 24, 2009, pp. 61-83.
U.S. Appl. No. 14/459,841, filed Aug. 14, 2014.
Sudakov-Boreysha et al, "ISFET CMOS Compatible Design and Encapsulation Challenges", Proceedings of the 2004 11th IEEE Electronics, Circuits and Systems, Dec. 13-15, 2004, pp. 535-538.
Nazarudin et al, "Characterization of Acrylate-based ChemFET Sensor for Nitrate Sensing and Monitoring", IEEE Conference on Biomedical Engineering and Sciences (IECBES), Dec. 8-10, 2014, pp. 154-158.

* cited by examiner

*Primary Examiner* — Ha Tran T Nguyen
*Assistant Examiner* — Jordan Klein
(74) *Attorney, Agent, or Firm* — Charlene R. Jacobsen

(57) ABSTRACT

A sensing device includes a sensor die having a sensing region formed at a first surface of the sensor die. The sensing device further includes an encapsulant covering the sensing die, the encapsulant having a cavity formed therein, wherein the cavity exposes the sensing region. A sensitive membrane material is deposited within the cavity over the sensing region. A method of manufacturing sensing devices entails mounting a plurality of sensing dies to a carrier, encapsulating the dies in an encapsulant, forming cavities in the encapsulant, the cavities exposing a sensing region of each sensor die, and depositing the sensitive membrane material within each of the cavities. The encapsulating and forming operations can be performed simultaneously using a film-assisted molding (FAM) process, and the depositing operation is performed following FAM at an ambient temperature that is lower than the temperature needed to perform FAM.

18 Claims, 5 Drawing Sheets

SENSING FIELD EFFECT TRANSISTOR DEVICES AND METHOD OF THEIR MANUFACTURE

TECHNICAL FIELD OF THE INVENTION

The present invention relates generally to semiconductor devices. More specifically, the present invention relates to sensing field effect transistors (SFETs) and a method of manufacturing SFETS.

BACKGROUND OF THE INVENTION

Field effect transistors (FETs) can be used in sensors configured to detect and analyze chemical substances and biological agents within fluids. Typically, these sensors rely on the voltage developed between the gate and a reference electrode. More particularly, changes in the gate bias result in a change in the channel current flowing through the device. In some designs, a fluid being sensed is in intimate contact with the gate dielectric. In other designs, the fluid being sensed is separated from the gate dielectric by a sensitive membrane or coating (e.g., a layer or coating applied to the gate dielectric). For example, depending on the application and the type of sensitive membrane or coating overlying the gate dielectric, these devices may be termed ion-sensitive field effect transistors (ISFETS), immunological field effect transistors (IMFETS), or enzyme field effect transistors (ENFETS).

Such sensor designs can include one or more sensors and one or more reference sensors integrated into one or more integrated circuit (IC) dies or chips. Unfortunately, the manufacturing process of such IC dies is relatively complex and costly to manufacture.

BRIEF DESCRIPTION OF THE DRAWINGS

The accompanying figures in which like reference numerals refer to identical or functionally similar elements throughout the separate views, the figures are not necessarily drawn to scale, and which together with the detailed description below are incorporated in and form part of the specification, serve to further illustrate various embodiments and to explain various principles and advantages all in accordance with the present invention.

DETAILED DESCRIPTION

In overview, the present disclosure concerns sensing devices (referred to below as SFET devices) and methods of their manufacture. The sensing device embodiments described herein each include at least one integrated circuit (IC) sensing die having at least one sensing region formed on a surface thereof. The sensing die is encapsulated in an encapsulant and one or more cavities are formed in the encapsulant to expose the sensing region. A sensitive membrane material is deposited in the one or more cavities. Encapsulation and cavity formation can be performed simultaneously using, for example, a film-assisted molding (FAM) process. The membrane material is susceptible to damage in elevated temperature conditions, such as those used for FAM. Thus, deposition of the sensitive membrane material can be performed in a significantly lower temperature environment following the FAM process. Additionally, the thickness of the sensitive membrane can be suitably controlled for optimal sensor reliability. Such methodology can yield improvements in sensor reliability, efficiency improvements in high volume manufacturing environments, and cost savings.

The instant disclosure is provided to further explain in an enabling fashion the best modes, at the time of the application, of making and using various embodiments in accordance with the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

Figure 1:
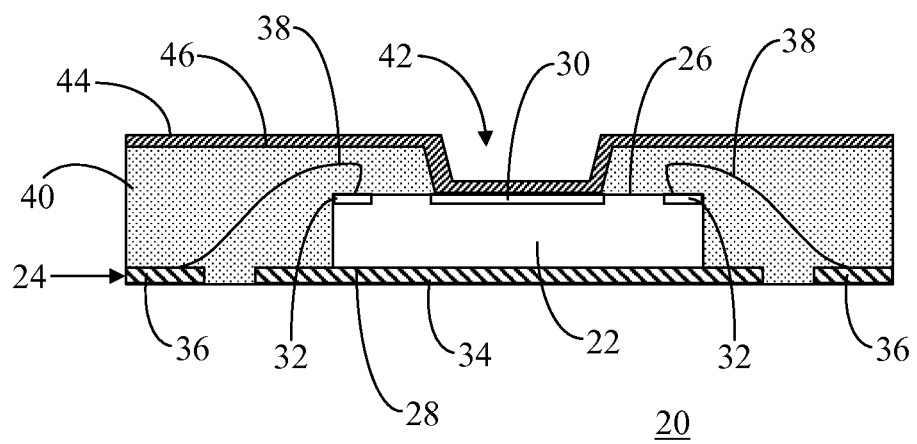
FIG. 1 shows a cross-sectional side view of a sensing device in accordance with an example embodiment.

Referring now to FIG. 1, FIG. 1 shows a cross-sectional side view of a sensing device 20 in accordance with an example embodiment. Sensing device 20 generally includes an integrated circuit (IC) sensing die 22 mounted upon a carrier 24 which may be, for example, a lead frame (discussed below). More particularly, sensing die 22 includes a first surface 26 and a second surface 28. One or more sensing regions 30 (one shown) are formed at first surface 26. Additionally, electrically conductive contacts 32 are formed at first surface 26. Second surface 28 is mounted to carrier 24 by, for example, adhesion to a mounting pad 34 of carrier 24. It should be understood that the use of relational terms, if any, such as first and second, top and bottom, and the like are used solely to distinguish one from another entity or action without necessarily requiring or implying any actual such relationship or order between such entities or actions.

Contacts 32 are electrically coupled to conductive pads 36 (which may be the leads of the lead frame) via electrically conductive interconnects 38, such as bond wires. Conductive pads 36 are laterally displaced from sensing die 22 and may surround one or more sides of sensing die 22. Sensing die 22, carrier 24 with conductive pads 36, and conductive interconnects 38 are covered by an encapsulant 40, such as a protective resin system. The term "protective resin system," may refer to a resin-cure catalyst system or to a molding compound, which may contain many constituents, for FAM. However, at least a portion (for example, the bottom surfaces) of conductive pads 36 may be exposed from encapsulant 40. Thus, conductive pads 36 can serve as inputs and/or outputs for accessing sensing die 22.

Encapsulant 40 protects the various components of sensing device 20 from exposure to external elements, e.g., air, moisture, liquids, and/or the substance of interest. Thus, encapsulant 40 provides robust mechanical and environmental protection. Furthermore, encapsulant 40 can act as a structural element in the final assembly. Encapsulant 40 may be formed in any suitable manner, as will be discussed in greater detail below, and any suitable molding material (e.g., epoxy- or silicon-based compounds) may be used. At least one cavity 42 (only one shown), having any suitable dimension or dimensions, is formed in encapsulant 40 to expose sensing region 30.

In an embodiment, sensing die 22 may include one or more ion-sensitive field effect transistors (ISFETs), immunological field effect transistors (IMFETs), enzyme field effect transistors (ENFETs), or other types of FETs that are affected by chemical substances and/or biological agents in a fluid that contacts the sensing electrodes or sensitive materials of the FETs. As such, sensing device 20 having sensing die 22 is generically referred to herein as a sensing FET device, i.e., SFET device 20. SFET device 20 may be incorporated into a system that is configured to detect and process the electrical signals produced by SFET device 20. Accordingly, such systems may produce measurement data indicating the presence of or representing the concentration of a chemical substance or biological agent in a fluid that is applied to the device.

In some configurations, sensing die 22 may include two sensing FETs that can provide differential signals. In other configurations, sensing die 22 may include a sensing FET and a reference FET. And in still other configurations, sensing die 22 may include two SFETs and a reference FET. As known to those skilled in the art, a sensing FET has a gate, source, and drain (not shown), where the gate is electrically coupled to a sensing electrode. In the illustrated configuration, sensing region 30 serves as the sensing electrode that is exposed by cavity 42.

In accordance with a particular embodiment, a sensitive membrane material 44 is deposited within cavity 42 over sensing region 30. Thus, sensitive membrane material 44 covers sensing region 30 (i.e., the sensing electrode). As shown in the illustrated embodiment of FIG. 1, sensitive membrane material 44 is deposited over a top surface 46 of encapsulant 40 and within cavity 42 over sensing region 30. Deposition of sensitive membrane material 44 may be performed using any suitable method such as, for example, spray, dip, spin-coating, and so forth following encapsulation of the components of SFET device 20.

Sensitive membrane material 44 may be, but is not limited to, one of a biological substance sensitive material, a pH sensitive material, a chemical sensitive material, and an ion sensitive material. More specifically, the sensitive membrane material 44 may be an ion selective membrane and may include one or more materials that are selected from silicon nitride, polyvinyl chloride (PVC) compounds (e.g., PVC-based membranes), acrylates, urethanes, an enzyme, an antibody, an antigen, ribonucleic acid (RNA), deoxyribonucleic acid (DNA), DNA-like fragments, epitopes, and cell receptors. Other suitable sensitive materials may be used in other embodiments.

When sensitive membrane material 44 is exposed to a substance (e.g., a fluid) being tested, a variable charge may be induced in sensitive membrane material 44. This variable charge affects a charge in sensing region 30, which in turn affects the charge on the gate of the SFET in sensing die 22 and the current flowing through a channel underlying the gate. Thus, a signal can be produced by sensing die 22 that is indicative of the substance being tested.

Figure 2:
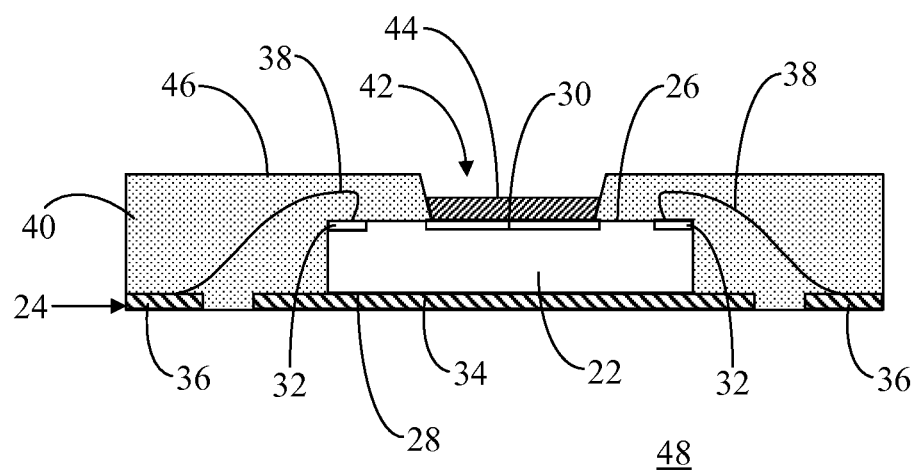
FIG. 2 shows a cross-sectional side view of an SFET device in accordance with another example embodiment.

FIG. 2 shows a cross-sectional side view of an SFET device 48 in accordance with an example embodiment. SFET device 48 includes many of the same features as SFET device 20 (FIG. 1). Therefore, the same reference numerals will be used to indicate the same or similar components. Accordingly, SFET device 48 includes sensing die 22 mounted upon carrier 24 and interconnects 38 formed between contacts 32 and the laterally displaced conductive pads 36. SFET device 48 also includes encapsulant 40 covering sensing die 22, carrier 24, and interconnects 38. Again, at least one cavity 42 is formed in encapsulant 40 to expose sensing region 30. However, in this example, sensitive membrane material 44 is only deposited within cavity 42 using, for example, a micro-dispenser. Thus, sensitive membrane material 44 is not deposited over top surface 46 of encapsulant 40.

Suitable membrane forming materials are relatively expensive. For example, some membrane forming materials may contain costly constituents such as ionophores, which facilitate ion transport by effectively increasing ionic permeability of membrane material 44. The embodiment of FIG. 2 has sensitive membrane material 44 only at sensor region 30, thereby eliminating waste of the costly sensitive membrane material 44.

Additionally, sensitive membrane material 44 can be formed to a preferred thickness within cavity 42. In some embodiments, a relatively thin layer of sensitive membrane material 44 may be desirable to yield a desired response time. That is, the ionophores in sensitive membrane material 44 pick up the ion of interest in the fluid being measured, and these loaded ionophores transport the ions across membrane 44 where they are sensed at the interface with sensor region 30. A relatively thin layer of sensitive membrane material 44 may enhance response time relative to a thicker layer of sensitive membrane material 44. Conversely, a thicker layer of sensitive membrane material 44 may be desirable where material 44 is being attacked or leached by the fluid being assayed. Such an attack may leach out the ionophores or even degrade the polymer, thereby effectively decreasing the sensitivity and/or functionality of sensing die 22.

Various materials used to form sensitive membrane material 44 are sensitive to high temperature conditions. For example, some of the materials are susceptible to damage at temperatures in excess of one hundred fifty degrees Celsius. Methodology discussed below yields the encapsulated sensing die 22 of SFET device 20 in which sensitive membrane material 44 is deposited following the encapsulation process at an ambient temperature that is less than one hundred fifty degrees Celsius so as to avoid damaging sensitive membrane material 44. Furthermore, the methodology discussed below enables the concurrent manufacture of an array of SFET devices by performing, for example, a film-assisted molding process. Since a FAM process may require exposure to temperatures in excess of one hundred and seventy degrees Celsius for upwards of five hours of combined molding and curing periods, sensitive membrane material 44 is deposited after the mold process to yield a plurality of SFET devices in a cost effective, high volume manufacturing environment.

Figure 3:
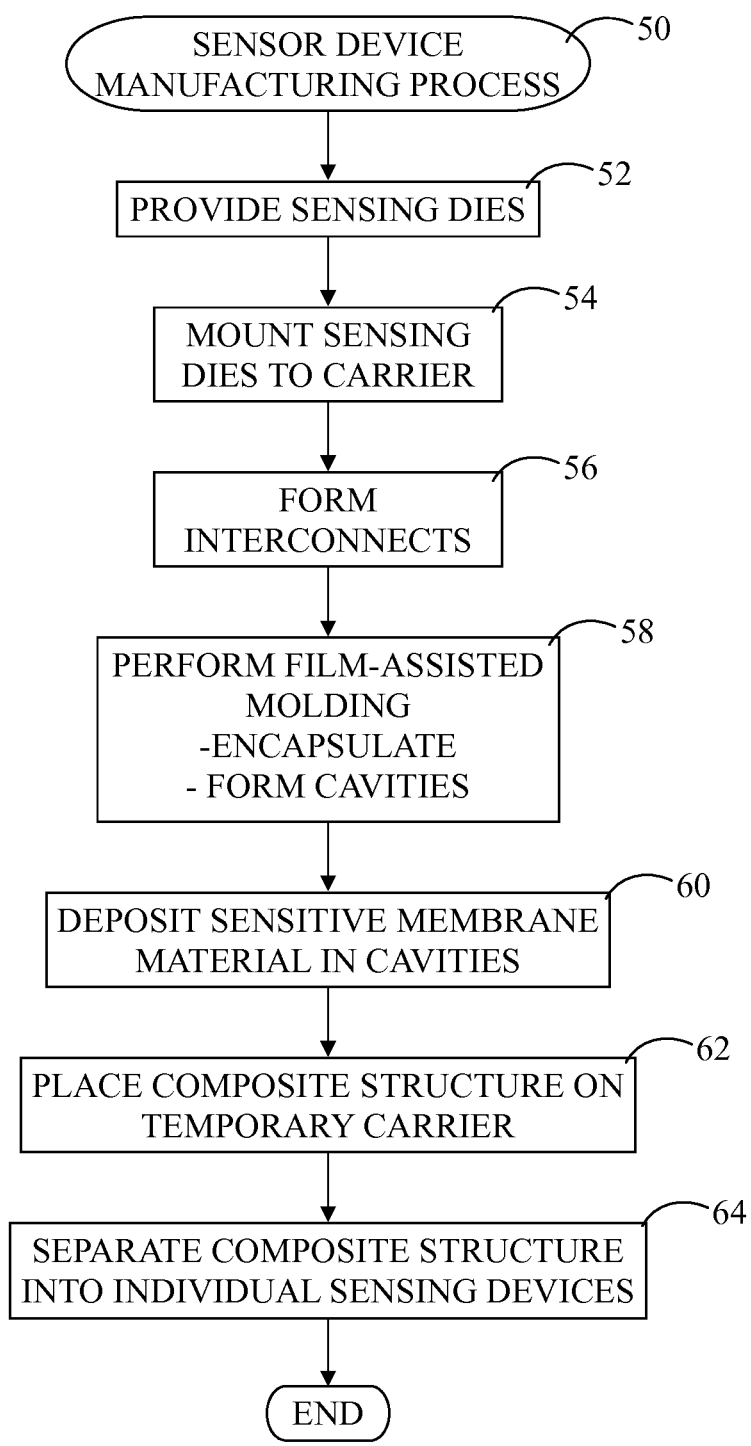
FIG. 3 shows a flowchart of a sensor device manufacturing process in accordance with an example embodiment.

FIG. 3 shows a flowchart of a sensor device manufacturing process 50 in accordance with an example embodiment. Sensor device manufacturing process 50 may be implemented in a high volume manufacturing environment to cost effectively produce reliable SFET devices 20. Process 50 is described in connection with manufacturing a plurality of SFET devices 20 and/or SFET devices 48. Hence, reference should be made to FIGS. 1-2 in connection with the following discussion of sensor device manufacturing process 50.

At a block 52 of sensor device manufacturing process 50, a plurality of sensing dies, such as sensing die 22, are provided. The sensing dies may be any of a plurality of design configurations that may include one or more ion-sensitive field effect transistors (ISFETs), immunological field effect transistors (IMFETs), enzyme field effect transistors (ENFETs), or other types of SFETs (i.e., sensing FETS) that are affected by chemical substances and/or biological agents in a fluid that contacts the sensitive membrane materials of the FETs. In an example, an SFET wafer may be fabricated that includes a plurality of SFET sensing dies. Thereafter, the SFET wafer undergoes a singulation processes (e.g., wet sawing, laser cutting, or the like) to form the plurality of separated sensing dies. Alternatively, the SFET wafer may be provided by an outside manufacturing facility. And in still other embodiments the separated SFET sensing dies may be provided by an outside manufacturing facility. In any event, sensitive membrane material 44 has not yet been deposited on the SFET wafer or on the singulated SFET sensing dies.

In a block 54, sensing dies 22 are mounted to carrier 24, such as a lead frame. Sensing dies 22 may be adhered, glued, or otherwise fixed to mounting pad 34 of carrier 24. In a block 56, electrically conductive interconnects 38 (e.g., bond wires) are formed between contacts 32 of sensing dies 22 and conductive pads 36 of carrier 24. In a block 58, carrier 24, sensing dies 22, and interconnects 38 are encapsulated in encapsulant 40 which may be, for example, a protective resin system. In a preferred embodiment, cavities 42 that expose sensing regions 30 at first surfaces 26 of the plurality of sensing dies 22 are formed simultaneously during the encapsulation process. This simultaneous formation may be performed using a film-assisted molding (FAM) process in which the mold comprises exclusion areas defining cavities 42.

In a film-assisted molding process, one or more plastic films are used to protect the die surface. This film is sucked down into the inner surfaces of the mold, before an electrically conductive sheet of carriers 24 (e.g., lead frames) having sensing dies 22 mounted thereon is loaded into the mold. Molding compound is first liquefied by heat (e.g., at a temperature in excess of one hundred fifty degrees Celsius) and pressure. The liquefied molding compound is forced into the closed mold cavities and is held there under additional heat and pressure until all of the molding material is solidified (i.e., cured). After opening the mold, the composite structure that includes the lead frame, sensing dies 22, and interconnects 38 covered by encapsulant 40 (i.e., the solidified molding compound) is unloaded. Thereafter, the composite structure is typically loaded into an oven for a final heated curing operation (e.g. at a temperature in excess of one hundred fifty degrees Celsius) that may last five to six hours, in order to complete the curing process.

Film-assisted molding offers a number of advantages over conventional transfer molding. These include the easy release of the encapsulated products from the mold and that the sensitive areas (such as sensing region 30) can be kept clear of the molding compound. Although a film-assisted molding process is discussed herein, it should be understood that alternative manufacturing processes may be contemplated. By way of example, cavities 42 may be formed after encapsulation by, for example, laser cutting in some embodiments. In other embodiments, cavities 42 may be formed with the use of cavity-defining mold structures. Cavity-defining mold structures include surfaces with a compliant material that serves to keep molding compound away from sensing region 30 and to protect sensing region 30 from mechanical damage.

Following encapsulation at block 58, sensitive membrane material 44 is deposited within cavities 42 at a block 60. With particular reference to FIG. 1, sensitive membrane material 44 may be deposited across top surface 46 of encapsulant 40 and within cavities 42 of the composite structure using, for example, a relatively inexpensive and efficient spray, dip, spin-coating or vapor/solution deposition process. With particular reference to FIG. 2, sensitive membrane material 44 may be deposited only within cavities 42 using, for example, a micro-dispensing process to attain the desired thickness of sensitive membrane material 44 within each of cavities 42.

The embodiments described and illustrated herein show formation of quad-flat no-lead (QFN) sensing device packages. However, in alternative embodiments, the sensing device packages may be a leaded sensing device package or a ball grid array (BGA) sensing package. In any sensing device package that includes a lead frame, e.g., carrier 24, the lead frame would need to be electroplated before device singulation, unless a pre-plated lead frame (e.g., a NiPdAu plated lead frame) is used. Accordingly, in a preferred embodiment, a pre-plated lead frame, e.g., carrier 24, may be used If the lead frame, e.g., carrier 24, is not pre-plated, a lead frame-based product may be plated with tin using an electrolytic process. Alternatively, another lead finish, e.g., Sn—Bi or another solderable finish, could also be electroplated. In some embodiments, electroplating may be performed following encapsulation at block 58. In such a scenario, the electroplating should be performed prior to deposition of sensitive membrane material 44 at block 60. Otherwise, sensitive membrane material 44 may become contaminated from the electroplating process. Accordingly, in other embodiments, sensitive membrane material 44 may be applied following electroplating. However, cavities 42 should be very thoroughly cleaned and dried after electroplating and before sensitive membrane material 44 is deposited at block 60.

In still other embodiments, electroplating process may be performed following deposition of sensitive membrane material 44 at block 60. In such a scenario, a plating tape may be applied to the surface of encapsulant 40 (i.e., the solidified molding compound) to keep the electroplating process material from contaminating sensitive membrane material 44.

Next, at a block 62, the composite structure may be placed on a temporary carrier, and at a block 64, the composite structure is separated into the individual SFET devices 20. Thereafter, SFET devices 20 can be removed from the temporary carrier and sensor device manufacturing process 50 ends. In some embodiments, the composite structure may be flipped before placement on the temporary carrier and the composite structure is separated from its backside into the individual SFET devices 20 in order to protect sensitive membrane material 44 from damage during the singulation process.

Sensor device manufacturing process 50 may be adapted for other embodiments that employ a mold-array process-ball grid array (MAPBGA). In a MAPBGA package, sensitive membrane material 44 would be applied after ball attach and laser marking in order to avoid the risk of contamination of sensitive membrane material 44 within each cavity 42 from laser marking. Thereafter, a MAPBGA composite structure may be inverted onto a temporary carrier, e.g., dicing tape, for saw singulation, e.g., separation, into the individual SEFET devices.

Figure 4:
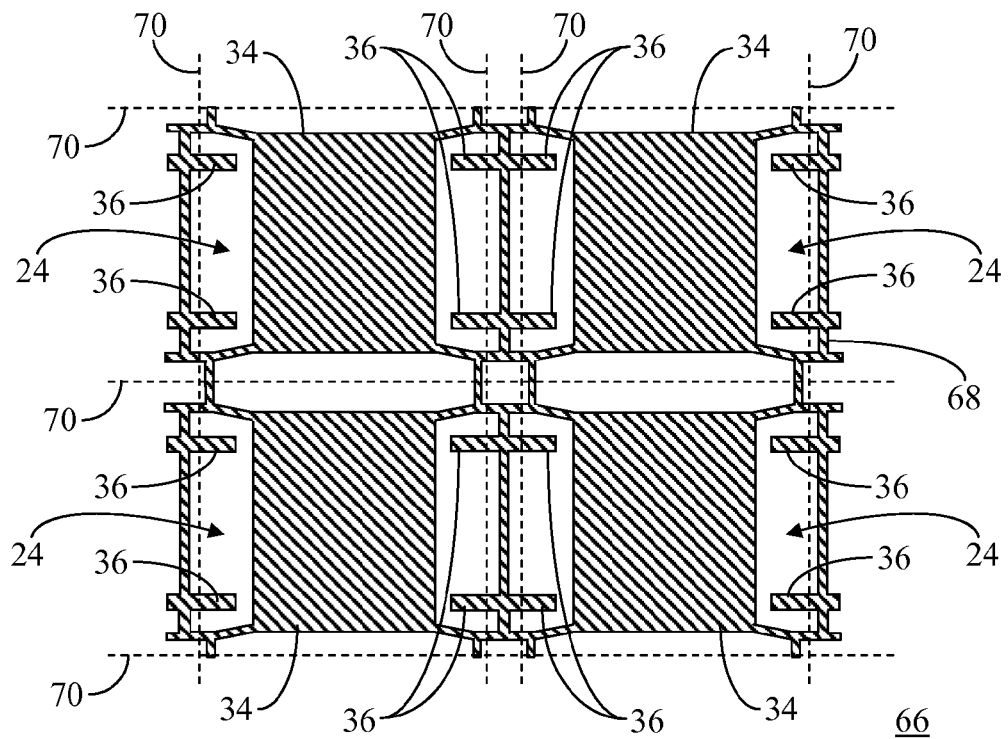
FIG. 4 shows a plan view of an electrically conductive sheet of lead frames that may be used to manufacture SFET devices in accordance with the method of FIG. 3.

FIG. 4 shows a plan view of an electrically conductive sheet 66, or strip, that includes a plurality of carriers 24, referred to hereinafter as lead frames 24. Conductive sheet 66 of lead frames 24 may be used to manufacture SFET devices 20 in accordance with sensor device manufacturing process 50 (FIG. 3). As shown, conductive sheet 66 includes multiple lead frames 24, each of which includes mounting pad 34 and conductive pads 36 (sometimes referred to as leads). The multiple lead frames 24 are interconnected by a frame structure 68, sometimes referred to as tie bars. During singulation, the composite structure which includes conductive sheet 66 will be diced, sawn, or otherwise singulated along dicing lines 70 so that lead frames 24 are mechanically and electrically separated from one another. Conductive sheet 66 is shown with only four lead frames 24 (each including one mounting pad 34 and their associated conductive pads 36) for simplicity of illustration. Those skilled in the art will readily recognize that a conductive sheet or strip of lead frames can include any number of mounting pads 34 and conductive pads 36 in accordance with a particular design configuration.

Figure 5:
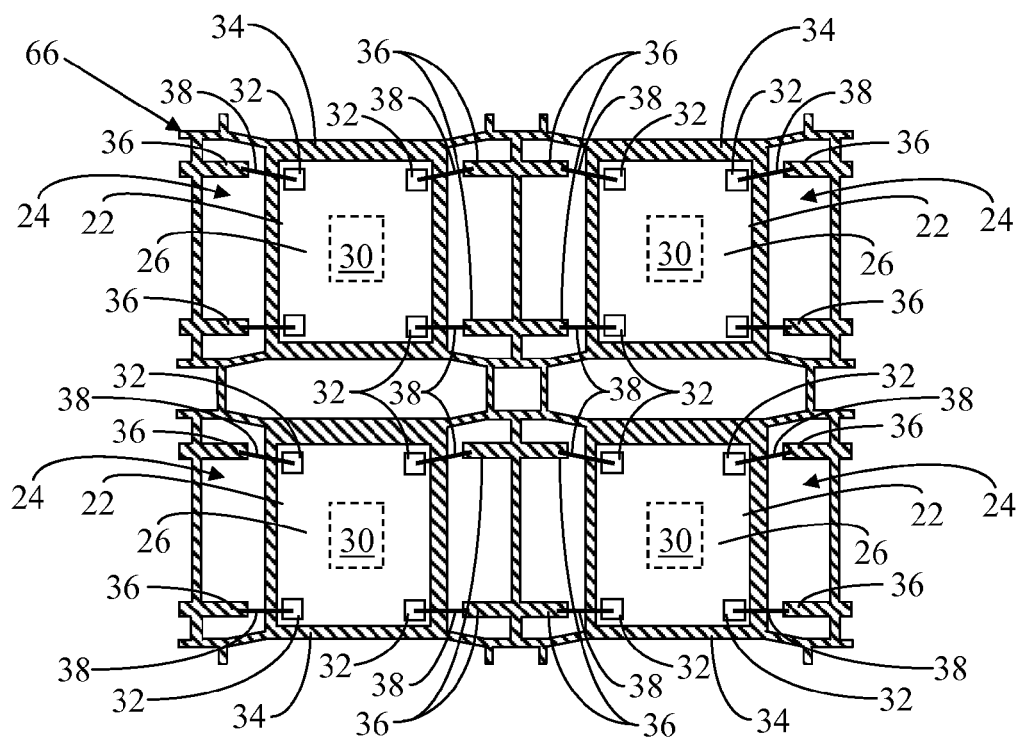
FIG. 5 shows a plan view of the conductive sheet of lead frames with sensor dies mounted to it in accordance with the method of FIG. 3.

Now referring to FIG. 5, FIG. 5 shows a plan view of conductive sheet 66 of lead frames 24 with sensor dies 22 mounted to it in accordance with sensor device manufacturing process 50 (FIG. 3). As shown in FIG. 5, sensor dies 22 are adhered, glued, or otherwise mounted to mounting pads 34 with first surfaces 26 of sensor dies 22 facing upwardly in the illustration. Thus, sensing regions 30 (represented by dashed line boxes) and contacts 32 at first surfaces 26 are exposed. Additionally, electrically conductive interconnects 38 have been formed between contacts 32 and conductive pads 36.

Figure 6:
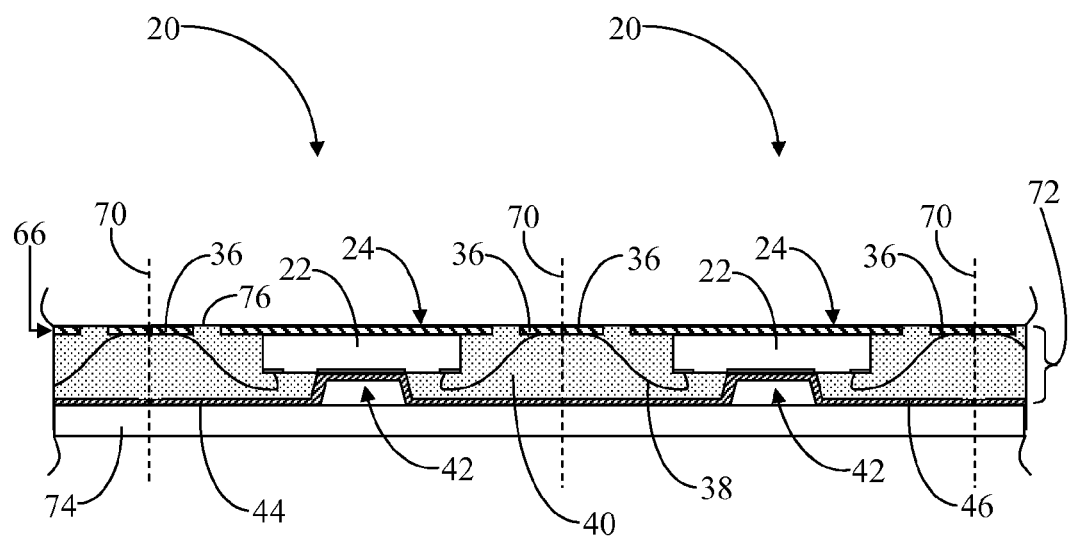
FIG. 6 shows a cross-sectional side view of a composite structure formed in accordance with the method of FIG. 3.

FIG. 6 shows a cross-sectional side view of a portion of a composite structure 72 formed in accordance with sensor device manufacturing process 50 (FIG. 3). Composite structure 72 includes conductive sheet 66 of lead frames 24 (as carriers) to which multiple sensing dies 22 (two shown) are mounted and interconnects 38, all of which is encapsulated or covered by encapsulant 40. SFET devices 20 of composite structure 72 correspond with the configuration of FIG. 1. Hence, SFET devices 20 include sensitive membrane material 44 deposited over top surface 46 of encapsulant 40 and within cavities 42. As shown, composite structure 72 is flipped and placed on a temporary carrier 74 with sensitive membrane material 44 facing temporary carrier 74. Thus, a backside 76 of composite structure 72 is exposed. Thereafter, composite structure 72 may undergo a singulation process from backside 76 along dicing lines 70 to separate composite structure 72 into a plurality of mechanically and electrically separated SFET devices 20.

Figure 7:
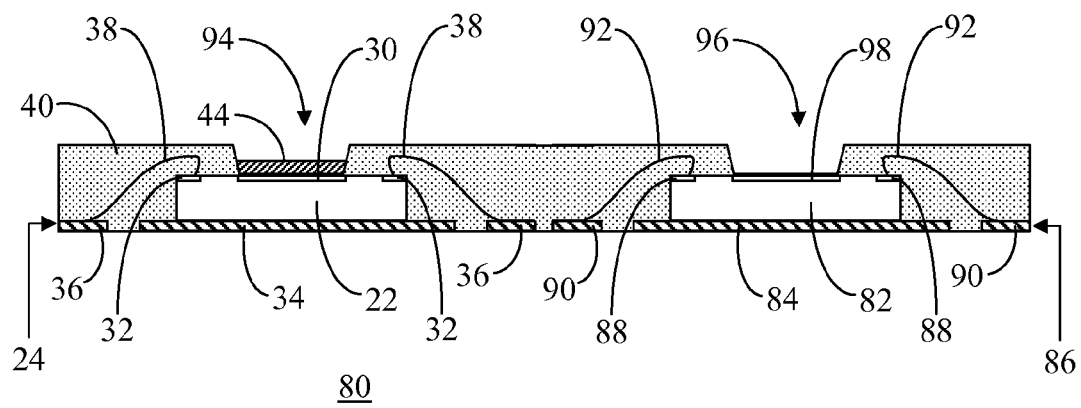
FIG. 7 shows a cross-sectional side view of an SFET device in accordance with another example embodiment.

Referring now to FIG. 7, FIG. 7 shows a cross-sectional side view of an SFET device 80 in accordance with another example embodiment. As mentioned briefly above, SFET devices can include various combinations and configurations of sensing and reference FETS. In this example, SFET device 80 includes sensing die 22 and a discrete reference FET die 82. Sensing die 22 is coupled to mounting pad 34 of lead frame 24, and generally includes one or more sensing regions 30 (one shown) and electrically conductive contacts 32 (previously described). Sensing die 22 is electrically coupled to conductive pads 36 of lead frame 24 vie electrically conductive interconnects 38.

Reference die 82 may be coupled to a mounting pad 84 of a carrier 86, and may have electrically conductive contacts 88 that are electrically coupled to conductive pads 90 of carrier 86 via electrically conductive interconnects 92. Reference die 82 is shown in representative form for simplicity. It should be understood, however, reference die 82 can encompass a great variation of designs, wiring configurations, through vias, and the like. Alternatively, reference die 82 may simply be embodied as an exposed metal strip that is external to sensing die 22. Additionally, carrier 86 need not be a separate structure from lead frame 24. Instead, each of sensing die 24 and reference die 82 may be coupled to the same carrier, or lead frame.

In any event, sensing die 22, carrier 24, conductive interconnects 38, reference die 82, carrier 86, and conductive interconnects 92 are largely covered by encapsulant 40, with at least a portion (for example, the bottom surfaces) of conductive pads 36 and conductive pads 90 being exposed from encapsulant 40 to serve as inputs and/or outputs. At least one cavity 94 (only one shown), having any suitable dimension or dimensions, is formed in encapsulant 40 to expose sensing region 30 of sensing die 22. Likewise, a cavity 96, having any suitable dimension, is formed in encapsulant 40 to expose a reference electrode 98 of reference die 82. It should be readily observed that sensitive membrane material 44 is deposited within cavity 94 over sensing region 30. However, sensitive membrane material 44 is not present in cavity 96 overlying reference electrode 98.

Sensor device manufacturing process 50 (FIG. 3) can be readily implemented to manufacture SFET device 80. For example, blocks 52, 54, 56 (FIG. 3) may be performed to provide dies 22, 82, mount dies 22, 82 to their respective carriers 24, 86, and form interconnects 38, 92. More specifically, the manufacturing methodology can entail providing an SFET wafer that includes a plurality of sensing dies 22, and separately providing a reference electrode wafer that includes a plurality of reference dies 82. Singulation processes (e.g., wet sawing, laser cutting, or the like) may be performed to separate the individual SFET IC dies 22 and the individual reference electrode dies 82. Thereafter, sensing dies 22 and references dies 82 may be suitably arranged and encapsulated using, for example, a film-assisted molding process, in order to form cavities 94, 96. Following encapsulation, sensitive membrane material 44 may be deposited in cavity 94, but not in cavity 96.

Figure 8:
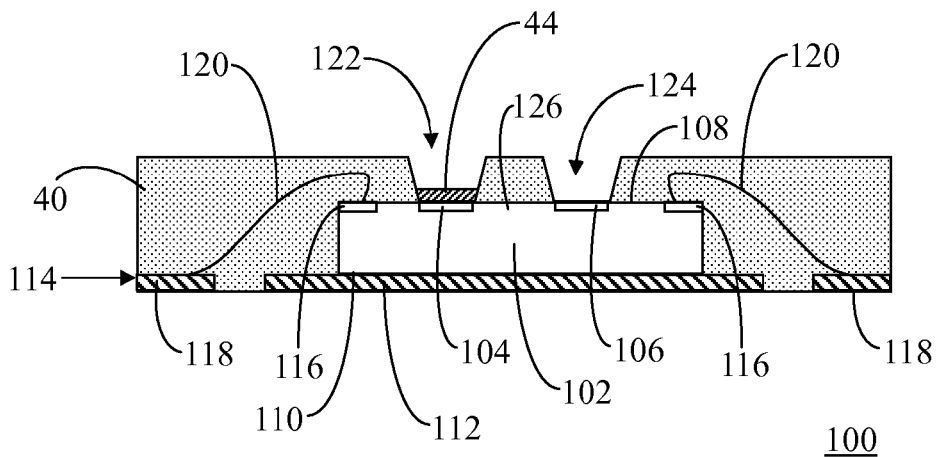
FIG. 8 shows a cross-sectional side view of an SFET device in accordance with another example embodiment.
Figure 9:
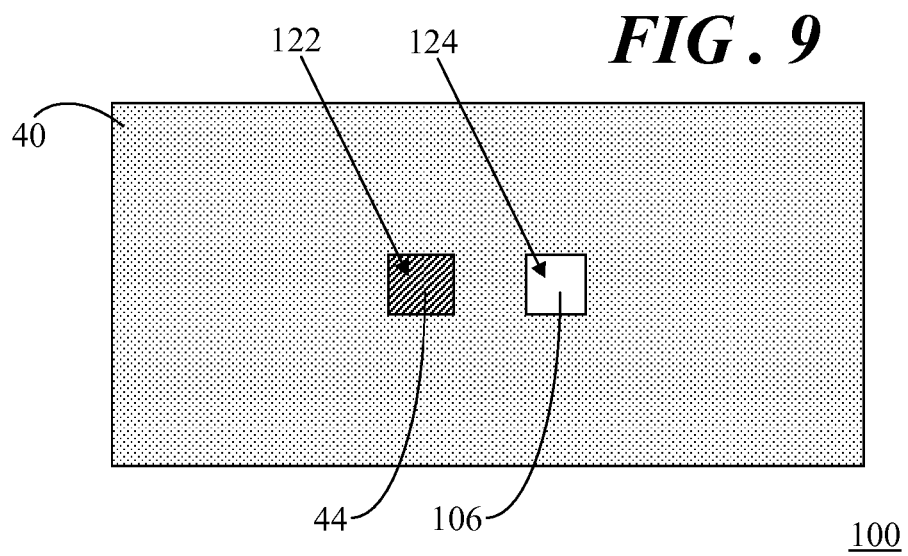
FIG. 9 shows a plan view of the SFET device of FIG. 8.

Referring to FIGS. 8-9, FIG. 8 shows a cross-sectional side view of an SFET device 100 in accordance with another example embodiment and FIG. 9 shows a plan view of SFET device 100. SFET device 100 includes a combined die 102. Combined die 102 generally includes a first SFET having a sensing region 104 and a second SFET or reference FET (REFET) having a reference electrode 106. Sensing region 104 and reference electrode 106 are formed at a first surface 108 of combined die 102 and a second surface 110 of combined die 102 is coupled to a mounting pad 112 of a carrier 114, e.g., a lead frame. First surface 108 further includes electrically conductive contacts 116 that are electrically coupled to conductive pads 118 (which may be the leads of the lead frame) via electrically conductive interconnects 120. Combined die 102, carrier 114, and conductive pads 118 are covered by encapsulant 40. Again, at least a portion (for example, the bottom surface) of conductive pads 118 is exposed from encapsulant 40.

At least one cavity 122 (only one shown), having any suitable dimension or dimensions, is formed in encapsulant 40 to expose sensing region 104 of combined die 102. Likewise, a cavity 124, having any suitable dimension, is formed in encapsulant 40 to expose reference electrode 106 of combined die 102. It should be readily observed that sensitive membrane material 44 is deposited within cavity 122 over sensing region 104. However, sensitive membrane material 44 is not present in cavity 124 overlying reference electrode 106.

Sensor device manufacturing process 50 (FIG. 3) can be readily implemented to manufacture SFET device 100. More specifically, the manufacturing methodology can entail providing an SFET wafer that includes a plurality of combined dies 102. A singulation process (e.g., wet sawing, laser cutting, or the like) may be performed to separate the individual combined dies 102. Combined dies 102 may be mounted to carriers 114 and conductive interconnects 120 may be formed. Thereafter, combined dies 102, carriers 114, and conductive interconnects 120 are encapsulated using, for example, a film-assisted molding process, in order to form cavities 122, 124. Following encapsulation, sensitive membrane material 44 may be deposited in cavity 122, but not in cavity 124.

SFET device 100 of FIGS. 8-9, includes separate cavities within encapsulant 40 in order to provide a convenient means for applying sensitive membrane material 44 over sensing region 104 without covering any portion of reference electrode 106 with sensitive membrane material 44. It should be readily observed, however, that the structure of FIGS. 8-9 requires a separation region 126 between sensing region 104 and reference electrode 106 that is sufficient to allow the molding of the distinct two cavities 122, 124. Thus, the two cavity configuration of SFET device 100 may result in an overall size of combined die 102 that is undesirably large in some embodiments.

Figure 10:
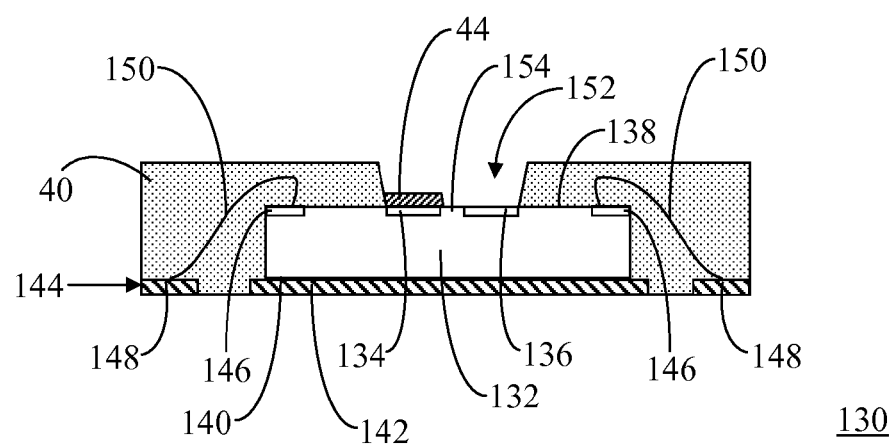
FIG. 10 shows a cross-sectional side view of an SFET device in accordance with another example embodiment.

Referring now to FIG. 10, FIG. 10 shows a cross-sectional side view of an SFET device 130 in accordance with another example embodiment. Like SFET device 100 of FIGS. 8-9, SFET device 130 includes a combined die 132. Combined die 132 generally includes a first SFET having a sensing region 134 and a second SFET or reference FET (REFET) having a reference electrode 136. Sensing region 134 and reference electrode 136 are formed at a first surface 138 of combined die 132. A second surface 140 of combined die 132 may be coupled to a mounting pad 142 of a carrier 144, e.g., a lead frame. First surface 138 further includes electrically conductive contacts 146 that are electrically coupled to conductive pads 148 (which may be the leads of the lead frame) via electrically conductive interconnects 150. Combined die 132, carrier 144, and conductive pads 148 are covered by encapsulant 40. Again, at least a portion (for example, the bottom surface) of conductive pads 148 is exposed from encapsulant 40.

SFET device 130 includes a single cavity 152, having any suitable dimension, formed in encapsulant 40 so as to expose both sensing region 134 and reference electrode 136 on first surface 138 of combined die 132. This structure allows combined die 132 to be smaller than combined die 102 (FIGS. 8-9) where sensing region 104 must be separated from reference electrode 106 by separation region 126. That is, a separation region 154 between sensing region 134 and reference electrode 136 can be smaller than separation region 126 since both sensing region 134 and reference electrode 136 are exposed in a single cavity 152. Accordingly, the single cavity structure of SFET device 130 enables combined die 132 to be smaller than combined die 102 of SFET device 100.

Sensitive membrane material 44 is deposited within cavity 152 overlying sensing region 134. However, sensitive membrane material 44 does not overlie reference electrode 136. That is, sensitive membrane material 44 is not desired on reference electrode 136 and methodology entails implementing any of various techniques, described below, to avoid leaving sensitive membrane material 44 on reference electrode 136 when sensitive membrane material 44 is deposited in cavity 152 overlying sensing region 134.

In some embodiments, sensitive membrane material 44 may be made from a photo-definable material, such as a photo-definable acrylate, a photo-definable urethane, or another suitable photo-definable material. A photo-definable material would be deposited within cavity 152 and, in some embodiments, over the top surface of encapsulant 40. Following deposition, the photo-definable material would be processed to prepare it for photo-imaging. This processing may require heating (sometimes called soft-backing) the photo-definable material to approximately 65-120 degrees Celsius for a predetermined period that may depend upon the thickness of the photo-definable material used to form sensitive membrane material 44. Typically, soft-baking takes between one and ten minutes.

After soft-bake, the photo-definable sensitive membrane material 44 may be exposed to appropriate light with the desired wavelength range, intensity, and level of collimation, through an appropriate photomask. After this exposure, photo-definable sensitive membrane material 44 may undergo a post-exposure bake at approximately 120 degrees Celsius. Following post-exposure bake, photo-definable sensitive membrane material 44 can then be developed in an aqueous or non-aqueous solvent to remove photo-definable sensitive membrane material 44 from undesired areas, such as over the surface of reference electrode 136. After removal of undesired material, sensitive membrane material 44 may undergo a hard bake, or post-development bake process to fully cure sensitive membrane material 44. Depending upon the choice of the photo-definable sensitive membrane material 44, one or both of the post-exposure bake and post-development bake may be eliminated.

Photo-definable sensitive membrane material 44 may also be removed from undesirable areas by other means. For example, the undesired material may be removed by optical means during the photo-imaging exposure process, if the photonic radiation is capable of decomposing the photo-definable sensitive membrane material 44 irradiated through the photomask. Alternatively, the undesired material may be removed using laser ablation at a selected point in the processing. And in still other embodiments, the undesired photo-definable sensitive membrane material 44 may be removed through the use of a mechanical mask and plasma processing. Other appropriate means to remove photo-definable sensitive membrane material 44 from undesired locations may also be used.

In other embodiments, the deposition of sensitive membrane material 44 may be suitably controlled. A technique for controlling the deposition of sensitive membrane material 44 may be to coat sensing region 134 with a material to facilitate wetting by a fluid form of sensitive membrane material 44. This material may be a hydrophilic material or another appropriate material. Since this material would at least initially exist at the interface of sensitive membrane material 44 and sensing region 134, the material that facilitates wetting must be compatible with sensitive membrane material 44 and its subsequent function. Another means to control the deposition of sensitive membrane material 44 may be to coat reference electrode 136 with a material that impedes wetting, such as a hydrophobic material, thus allowing sensitive membrane material 44, in fluid form, to wet and coat sensing region 134, but not reference electrode 136. If desired, the material that impedes wetting may be removed from reference electrode 136 after fully processing sensitive membrane coating 44 on sensing region 134. It may be necessary to apply the coating material that facilitates or impedes wetting while the SFET die are in wafer form to simplify application of the materials, possibly by spin-coating, and the removal of the coating material, from undesirable locations, possibly by photo-lithographic processing, or other appropriate means.

Accordingly, embodiments described herein entail sensing devices and methods of their manufacture. An embodiment of a method of forming a sensing device comprises providing a sensing die having a first surface and a sensing region formed at the first surface, encapsulating the sensing die in an encapsulant, forming a cavity in the encapsulant, the cavity exposing the sensing region, and depositing a sensitive membrane material within the cavity over the sensing region.

A embodiment of a method of forming a plurality of sensing devices comprises providing a plurality of integrated circuit (IC) dies, each of the sensing dies having a first surface, a second surface, and a sensing region formed at the first surface, and mounting the plurality of sensing dies to a carrier such that the second surface of each of the sensing dies is coupled to the carrier. The method further comprises concurrently encapsulating each of the sensing dies mounted to the carrier in an encapsulant to form a composite structure, the encapsulant covering the sensing dies and the carrier, forming cavities in the encapsulant, one each of the cavities exposing the sensing region of each of the sensing dies, depositing a sensitive membrane material within each of the cavities over the sensing region, placing the composite structure on a temporary carrier with the sensitive membrane material facing the temporary carrier such that a backside of the composite structure is exposed, and separating the composite structure from the backside into the plurality of sensing devices.

An embodiment of a sensing device comprises an integrated circuit (IC) die having a first surface and a sensing region formed at the first surface, an encapsulant covering the sensing die, the encapsulant having a cavity formed therein, the cavity exposing the sensing region, and a sensitive membrane material deposited within the cavity over the sensing region.

The sensing device embodiments described herein each include at least one sensing die having a sensing region formed on a surface thereof. The sensing die is encapsulated in an encapsulant and one or more cavities are formed in the encapsulant to expose the sensing region. A sensitive membrane material is deposited in the one or more cavities. Encapsulation and cavity formation can be performed simultaneously using, for example, a film-assisted molding (FAM) process. The membrane material is susceptible to damage in elevated temperature conditions, such as those used for FAM. Thus, deposition of the sensitive membrane material can be performed in a significantly lower temperature environment following the FAM process. Additionally, the thickness of the sensitive membrane can be suitably controlled for optimal sensor reliability. Such methodology can yield improvements in sensor reliability, efficiency improvements in high volume manufacturing environments, and cost savings.

This disclosure is intended to explain how to fashion and use various embodiments in accordance with the invention rather than to limit the true, intended, and fair scope and spirit thereof. The foregoing description is not intended to be exhaustive or to limit the invention to the precise form disclosed. Modifications or variations are possible in light of the above teachings. The embodiment(s) was chosen and described to provide the best illustration of the principles of the invention and its practical application, and to enable one of ordinary skill in the art to utilize the invention in various embodiments and with various modifications as are suited to the particular use contemplated. All such modifications and variations are within the scope of the invention as determined by the appended claims, as may be amended during the pendency of this application for patent, and all equivalents thereof, when interpreted in accordance with the breadth to which they are fairly, legally, and equitably entitled.

What is claimed is:

1. A method of forming a sensing device comprising:
providing a sensing die having a first surface and a sensing region formed at said first surface;
encapsulating said sensing die in an encapsulant, said encapsulating process being performed at a temperature in excess of one hundred fifty degrees Celsius;
forming a cavity in said encapsulant, said cavity exposing said sensing region; and
depositing a sensitive membrane material within said cavity over said sensing region, wherein said sensitive membrane material is susceptible to damage at said temperature in excess of one hundred fifty degrees Celsius, and said depositing operation is performed following said encapsulating operation at an ambient temperature that is less than one hundred fifty degrees Celsius.

2. The method of claim 1 further comprising mounting a second surface of said sensing die to a carrier prior to said encapsulating, said second surface being on an opposite side of said sensing die from said first surface.

3. The method of claim 1 wherein said sensing die includes contacts on said first surface, and said method further comprises forming electrically conductive interconnects between said contacts and conductive pads laterally displaced from said sensing die prior to said encapsulating.

4. The method of claim 1 wherein said encapsulating and forming operations are performed simultaneously.

5. The method of claim 1 further comprising performing a film-assisted molding process to simultaneously perform said encapsulating and forming operations.

6. The method of claim 1 wherein said depositing operation comprises depositing a layer of said sensitive membrane material over a top surface of said encapsulant and within said cavity.

7. The method of claim 1 wherein said depositing operation comprises depositing said sensitive membrane material only within said cavity.

8. A method of forming a sensing device comprising:
providing a sensing die having a first surface and a sensing region formed at said first surface;
providing a reference electrode;
forming a first cavity in said encapsulant, said first cavity exposing said sensing region;
forming a second cavity in said encapsulant, said second cavity exposing said reference electrode;
depositing a sensitive membrane material within said first cavity over said sensing region; and
abstaining from depositing said sensitive membrane material within said second cavity over said reference electrode.

9. A method of forming a plurality of sensing devices comprising:

providing a plurality sensing dies, each of said sensing dies having a first surface, a second surface, and a sensing region formed at said first surface;

mounting each of said plurality of sensing dies to a carrier such that said second surface of said each of said sensing dies is coupled to said carrier;

concurrently encapsulating said each of said sensing dies mounted to said carrier in an encapsulant to form a composite structure, said encapsulant covering said sensing dies and said carrier;

forming cavities in said encapsulant, one each of said cavities exposing said sensing region of said each of said sensing dies;

depositing a sensitive membrane material within said each of said cavities over said sensing region;

placing said composite structure on a temporary carrier with said sensitive membrane material facing said temporary carrier such that a backside of said composite structure is exposed; and separating said composite structure from said backside into said plurality of sensing devices.

10. The method of claim 9 further comprising:
performing a film-assisted molding process to simultaneously perform said encapsulating and forming operations, said film-assisted molding process being performed at a temperature in excess of one hundred fifty degrees Celsius, wherein said sensitive membrane material is susceptible to damage at said temperature in excess of one hundred fifty degrees Celsius; and said depositing operation is performed following said film-assisted molding process at an ambient temperature that is less than one hundred fifty degrees Celsius.

11. The method of claim 9 wherein said depositing operation comprises depositing a layer of said sensitive membrane material over a top surface of said encapsulant and within said each of said cavities.

12. The method of claim 9 wherein said depositing operation comprises depositing said sensitive membrane material only within said each of said cavities.

13. A sensing device comprising:
a sensing die having a first surface and a sensing region formed at said first surface;
a reference electrode;
an encapsulant covering said sensing die, said encapsulant having a first cavity formed therein, said first cavity exposing said sensing region, and said encapsulant having a second cavity formed therein to expose said reference electrode; and
a sensitive membrane material deposited within said first cavity over said sensing region, said sensitive membrane material being absent from said second cavity.

14. The sensing device of claim 13 further comprising a carrier upon which a second surface of said sensing die is mounted, said second surface being on an opposite side of said sensing die from said first surface, said encapsulant covering said carrier.

15. The sensing device of claim 13 further comprising:
conductive pads laterally displaced from said sensing die; and
electrically conductive interconnects coupled between contacts on said first surface of said sensing die and said conductive pads, said encapsulant covering said conductive pads and said electrically conductive interconnects.

16. The sensing device of claim 13 wherein said sensitive membrane material includes material that is susceptible to damage at a temperature in excess of one hundred fifty degrees Celsius.

17. The sensing device of claim 13 wherein said sensitive membrane material is selected from a biological material sensitive material, a pH sensitive material, a chemical sensitive material, and an ion sensitive material.

18. A sensing device comprising:
a sensing die having a first surface and a sensing region formed at said first surface;
an encapsulant covering said sensing die, said encapsulant having a cavity formed therein, said cavity exposing said sensing region; and
a sensitive membrane material deposited within said cavity over said sensing region, wherein said sensing device comprises a sensing field effect transistor (SFET), said sensing region of said SFET includes a sensing electrode exposed by said cavity, and said sensitive membrane material covers said sensing electrode, wherein said sensitive membrane material is configured to induce a variable charge when said sensitive membrane material is exposed to an agent to which said sensitive membrane material is sensitive, said variable charge affecting a charge on said sensing electrode.

* * * * *